United States Patent [19]

Malz, Jr.

[11] Patent Number: 4,814,504

[45] Date of Patent: Mar. 21, 1989

[54] PROCESS FOR THE PRODUCTION OF DIPHENYLAMINE

[75] Inventor: Russell E. Malz, Jr., Naugatuck, Conn.

[73] Assignee: Uniroyal Chemical Company, Inc., Middlebury, Conn.

[21] Appl. No.: 903,354

[22] Filed: Sep. 3, 1986

[51] Int. Cl.$^4$ .............................................. C07C 87/54
[52] U.S. Cl. .................................... 564/435; 564/433; 502/355
[58] Field of Search ................................ 564/435, 433

[56] References Cited

U.S. PATENT DOCUMENTS 3,118,944  1/1964  Addis .................................... 564/435

FOREIGN PATENT DOCUMENTS

60/51152  3/1985  Japan ...................................... 564/435
1402707  8/1975  United Kingdom .

OTHER PUBLICATIONS

Kirk-Othmer, Encyclopedia of Chemical Technology, vol. 2, p. 311 (3d Ed., 1978).
H. Rootare, "A Short Literature Review of Mercury Porosimetry", Aminco Laboratory News, pp. 4A-4H, 1968.
Ogasawasa, S., *J. of Catalysis*, vol. 25, pp. 105-110 (1972).
Ogasawasa, S., *J. of Catalysis*, vol. 29, pp. 67-74 (1973).

*Primary Examiner*—Glennon H. Hollrah
*Assistant Examiner*—Susan Treanor
*Attorney, Agent, or Firm*—Raymond D. Thompson

[57] ABSTRACT

Diphenylamine is produced by contacting aniline with an alumina catalyst having at least about 30 percent by volume of its total porosity in the form of pores having a diameter of between about 120 and about 200 Angstroms and a sulfur content, as measured in the form of $SO_4$, of less than about 0.02 percent by weight at between about 380° and 475° C.

6 Claims, No Drawings

PROCESS FOR THE PRODUCTION OF DIPHENYLAMINE

FIELD OF THE INVENTION

This invention is directed to an improved process for the production of diphenylamine from aniline, which process involves the use of an alumina catalyst having at least about 30 percent by volume of its total porosity in the form of pores having a diameter of between about 120 and about 200 Angstroms and a sulfur content, as measured in the form of $SO_4$, of less than about 0.02 percent by weight.

BACKGROUND OF THE INVENTION

Diphenylamine is well known to have a variety of uses, including as a rubber antioxidant and accelerator, a stabilizer for plastics, as well as an intermediate for pesticides, explosives, dyes and antioxidants. Conventionally, diphenylamine is produced by contacting aniline with an alumina catalyst at very high temperatures of more than 450° C. Thus, Kirk-Othmer, Encyclopedia of Chemical Technology, Vol. 2, page 311 (3d Ed., 1978) discloses that "Passing aniline vapor over activated alumina under pressure and at a temperature above 450° C. gives diphenylamine".

Somewhat similarly, U.S. Pat. No. 3,118,944 to Addis discloses a process for producing diphenylamine by reacting aniline with an alumina catalyst having a surface area of some 100–400 square meters per gram and a pore volume of about 0.50 cubic centimeters per gram. It is particularly noteworthy that Addis indicates (at Col. 3, lines 32–33) that "However at appreciably below 450° the result is too poor to be useful".

Conventional commercial processes typically employ alumina catalysts having more than one-third of their total porosity (by volume) in the form of comparatively small pores (having a diameter of between about 36 and about 60 Angstroms) and an initial sulfur content (as measured in the form of $SO_4$) in excess of 3 weight percent. Typically, however, such sulfur content may decrease during the reaction process.

Although such known processes are effective in converting aniline into diphenylamine (and ammonia) at yields of up to about 90% (based upon the conversion of aniline), it would nonetheless be desirable to possess a process for producing diphenylamine from aniline at increased efficiency.

Moreover, it is evident that such high temperature prior art processes require the consumption of relatively large amounts of energy and are thus economically undesirable. Thus, it would be desirable to possess a process for producing diphenylamine which required reduced amounts of energy or alternatively, which produced diphenylamine more efficiently at such higher temperatures.

Accordingly, it is an object of this invention to provide a process for the production of diphenylamine from aniline, which process exhibits increased efficiency of conversion.

It is a further object of this invention to provide a process for the production of diphenylamine, which process requires reduced amounts of energy consumption to produce a given amount of product.

The above objects and additional objects will become more fully apparent from the following description and accompanying Examples.

DESCRIPTION OF THE INVENTION

This invention is directed to a process for producing diphenylamine comprising contacting aniline with an alumina catalyst having at least about 30 volume percent of its total porosity in the form of pores having a diameter of between about 120 and about 200 Angstroms and a sulfur content, as measured in the form of $SO_4$, of less than about 0.02 percent by weight.

The alumina catalyst employed in the process of this invention possesses at least about 30 percent, preferably at least about 40 percent, and most preferably at least about 50 percent, by volume of its porosity in the form of pores having a diameter of between about 120 and about 200 Angstroms. As is employed herein, the term "diameter" means the mean pore diameter as determined by mercury porosimetry. See, e.g., H. Rootare, "A Short Literature Review of Mercury Porosimetry, Aminco Laboratory News, pp. 4A–4H, 1968.

Furthermore, the catalyst employed in the process of this invention possesses a sulfur content, as measured in the form of $SO_4$, of less than about 0.02 percent by weight.

According to the process of this invention, diphenylamine is produced by contacting aniline with the alumina catalyst described above typically at between about 380° and about 470° C., preferably at between about 400° and about 465° C., to produce diphenylamine and ammonia according to the following reaction:

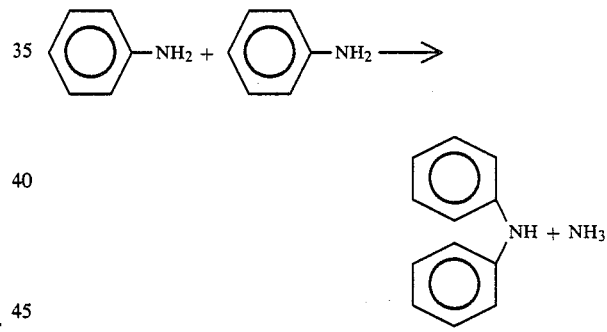

Reaction presure may range from subatmospheric to superatmospheric, with pressures ranging from atmospheric to 10 psig being preferred.

The process of this invention is typically performed as follows. The reactor, typically composed of steel and containing a catalyst bed, is preheated to the reaction temperature. The aniline is metered in, typically at a rate such that contact is maintained with the catalyst bed for a period of between about 1 and about 2 minutes, although longer and shorter contact times may be employed.

The diphenylamine product may then be isolated from the resultant reactor mixture by means well known to those skilled in the art, usually by distillation. If desired, the unreacted aniline may be isolated from the reaction mixture and recycled.

The alumina catalyst may be initially activated or reactivated periodically by treatment with boron trifluoride according to processes well known to those skilled in the art. Typically such treatment involves passing an aniline stream containing $BF_3$-aniline salt or gaseous $BF_3$ in amounts of up to about 0.5 percent by weight based upon the weight of aniline in the stream.

Further, the alumina catalyst may be periodically regenerated by heating such catalyst, typically in the presence of air, to between about 500° C. and about 625° C. in order to burn off accumulated tars.

The process of this invention produces diphenylamine in greater efficiencies and at lower temperatures than do present commercial diphenylamine processes.

EXAMPLES

The following Examples are intended to further illustrate the present invention and are not intended to limit the scope of the invention in any manner whatsoever.

EXAMPLES 1 AND 2 AND COMPARATIVE EXPERIMENTS A and B

In order to compare the process of this invention with a commercially employed process for producing diphenylamine from aniline several runs were conducted with alumina that had been pretreated with $BF_3$, by treating them with a stream of aniline containing about 0.2 weight percent of aniline-boron fluoride salt at the reaction temperature listed below. These runs were conducted in a reactor (a Chemical Data Systems Micro Pilot Plant Model 8040) which was a 12" by 1" tube equipped with a central well containing six thermocouples positioned throughout the bed and heated by three independent heaters. The reactor was maintained at the temperature indicated in Table I for each run as indicated. In all runs, the central well contained a 50 gram charge of catalyst.

Furthermore, in all runs aniline was metered in at a WHSV (weight hourly space velocity—equal to the weight of aniline per hour divided by the weight of catalyst) of 0.11. The aniline was contacted with the catalyst for about 1.5 minutes.

The catalysts employed in Examples 1 and 2 and in Comparative Experiments A and B posessed the following initial characteristics:

| | Surface Area (m²/g) | |
|---|---|---|
| Pore Volume* (cc/gram) | 184 Examples 1 and 2 | 299 Comparative Experiments A and B |
| Up to: 36Å | 0.009 | 0.095 |
| 60Å | 0.014 | 0.299 |
| 90Å | 0.083 | 0.325 |
| 120Å | 0.199 | 0.331 |
| 200Å | 0.687 | 0.339 |
| 350Å | 0.715 | 0.349 |
| 600Å | 0.726 | 0.367 |
| 1,000Å | 0.733 | 0.395 |
| 5,000Å | 0.734 | 0.488 |
| 10,000Å | 0.734 | 0.512 |
| 115,300Å | 0.734 | 0.540 |
| $SO_4$ (wt. %) | 0.01 | 3.7 |

*As measured by Mercury porosimetry.

The resulting diphenylamine streams were analyzed by gas liquid chromatography utilizing a Varian 8700 by comparison with an internal standard. Several runs were made for each Example and Comparative Experiment. The mean values obtained for each example and Comparative Experiment are listed in Table I.

| | Example or Comparative Experiment | | | |
|---|---|---|---|---|
| | 1 | 2 | A | B |
| Reaction Temperature (°C.) | 400 | 450 | 425 | 450 |
| Yield[1] | 94 | 98 | 90 | 90 |
| Conversion[2] | 41 | 44 | 32 | 36 |

Remarks
[1] Yield = (2 times the number of moles of diphenylamine produced divided by the number of moles of aniline consumed) times 100.
[2] Conversion = (2 times the number of moles of diphenylamine produced divided by the number of moles of aniline in) times 100.

The above data indicate the unexpectly increased yields and conversions achieved by the process of his invention. Particularily noteworthy is the fact that a comparison of Example 1 with Comparative Experiment B indicates that the process of this invention provides increased yields a temperature 50° C. below that of commercially employed diphenylamine production processes.

EXAMPLE 3

Employing the same reaction employed in Example 1, several additional runs were made at a temperature of 450° C. following the procedure of Example 1, except that the catalyst (which was identical to that employed in Examples 1 and 2) was not pretreated with boron trifluoride. The average yield of diphenylamine was 86 percent and the average conversion 36 percent. This indicates that in the process of the present invention no $BF_3$ pretreatment—a required step in commercial diphenylamine processes—is required.

What is claimed is:

1. A process for producing diphenylamine comprising contacting aniline with an alumina catalyst having at least about 30 percent by volume of its total porosity in the form of pores having a diameter of between about 120 and about 200 Angstroms and a sulfur content, as measured in the form of $SO_4$, of less than about 0.02 percent by weight, which catalyst has been pretreated with at least one member selected from the group consisting of boron trifluoride and boron trifluoride-aniline salt.

2. The process of claim 1 wherein said process is conducted at between about 380° and about 475° C.

3. The process of claim 2 wherein said process is conducted at between about 400° and about 465° C.

4. The process of claim 1 wherein said catalyst has at least about 40 percent by volume of its total porosity in the form of pores having a diameter of between about 120 and about 200 Angstroms.

5. The process of claim 1 wherein said catalyst has at least about 50 percent by volume of its total porosity in the form of pores having a diameter of between about 120 and about 200 Angstroms.

6. A process for producing diphenylamine comprising the steps:
    A. Pretreating a catalyst having at least about 50 percent by volume of its total porosity in the form of pores having and a diameter of between about 120 and about 200 Angstroms and a sulfur content, in the form of $SO_4$, of less than about 0.02 percent by weight, with at least one member selected from the group consisting of boron trifluoride and boron trifluoride-aniline salt; and
    B. Contacting aniline with such treated catalyst at between about 400° and about 465° C.

* * * * *